(12) United States Patent
O'Reilly et al.

(10) Patent No.: US 10,285,593 B2
(45) Date of Patent: May 14, 2019

(54) METHOD FOR REGISTERING PRE-OPERATIVE IMAGES OF A SUBJECT TO AN ULTRASOUND TREATMENT SPACE

(71) Applicant: Sunnybrook Research Institute, Toronto, ON (CA)

(72) Inventors: Meaghan O'Reilly, Scarborough (CA); Kullervo Hynynen, Toronto (CA); Ryan Jones, Toronto (CA)

(73) Assignee: Sunnybrook Research Institute, Toronto, ON (CA)

( * ) Notice: Subject to any disclaimer, the term of this patent is extended or adjusted under 35 U.S.C. 154(b) by 18 days.

(21) Appl. No.: 15/564,308

(22) PCT Filed: Apr. 25, 2016

(86) PCT No.: PCT/IB2016/000627
§ 371 (c)(1),
(2) Date: Oct. 4, 2017

(87) PCT Pub. No.: WO2016/170427
PCT Pub. Date: Oct. 27, 2016

(65) Prior Publication Data
US 2018/0132723 A1 May 17, 2018

Related U.S. Application Data

(60) Provisional application No. 62/152,565, filed on Apr. 24, 2015.

(51) Int. Cl.
*A61B 5/00* (2006.01)
*A61B 6/00* (2006.01)
(Continued)

(52) U.S. Cl.
CPC .......... *A61B 5/0042* (2013.01); *A61B 5/0035* (2013.01); *A61B 5/0037* (2013.01);
(Continued)

(58) Field of Classification Search
None
See application file for complete search history.

(56) References Cited

U.S. PATENT DOCUMENTS

2004/0236220 A1 11/2004 Willis
2008/0248419 A1 10/2008 Hirano
(Continued)

FOREIGN PATENT DOCUMENTS

WO 2014134188 A1 9/2014

OTHER PUBLICATIONS

International Search Report & Written Opinion; PCT/IB2016/000627; dated Sep. 14, 2016; 10 pages.

*Primary Examiner* — Idowu O Osifade
(74) *Attorney, Agent, or Firm* — Quarles & Brady LLP

(57) ABSTRACT

Systems and methods for registering pre-operative medical images, such as computed tomography ("CT") images, to the coordinate space of an ultrasound treatment system are provided. The registration is generally based on minimizing distances between locations associated with an anatomical feature, as identified from the medical images, and spherical surfaces defined by time-of-flight measurements for ultrasound data acquired from the anatomical feature by transducer elements. The locations associated with the anatomical feature, which may be a skull of the subject, can be points or planar surfaces define on the anatomical feature. The registration methods described here can be useful for aberration correction and targeting using an array of high-frequency ultrasound elements. In combination with cavitation monitoring and control, this ultrasound-based registration of CT images could eliminate the need for MRI during these treatments.

14 Claims, 6 Drawing Sheets

(51) Int. Cl.
| | | |
|---|---|---|
| *A61B 6/03* | (2006.01) | |
| *A61B 8/00* | (2006.01) | |
| *A61B 8/08* | (2006.01) | |
| *A61B 8/13* | (2006.01) | |
| *A61N 7/00* | (2006.01) | |
| *A61N 7/02* | (2006.01) | |
| *G06T 7/10* | (2017.01) | |
| *G06T 7/30* | (2017.01) | |
| *G06T 7/33* | (2017.01) | |
| *G06T 7/73* | (2017.01) | |
| *A61B 5/055* | (2006.01) | |
| *A61B 90/00* | (2016.01) | |

(52) U.S. Cl.
CPC ............... *A61B 5/055* (2013.01); *A61B 6/03* (2013.01); *A61B 6/032* (2013.01); *A61B 6/501* (2013.01); *A61B 6/5247* (2013.01); *A61B 8/0808* (2013.01); *A61B 8/13* (2013.01); *A61B 8/5261* (2013.01); *A61B 90/36* (2016.02); *A61N 7/00* (2013.01); *A61N 7/02* (2013.01); *G06T 7/10* (2017.01); *G06T 7/30* (2017.01); *G06T 7/33* (2017.01); *G06T 7/73* (2017.01); *A61B 8/4488* (2013.01); *A61B 2090/364* (2016.02); *G06T 2207/10028* (2013.01); *G06T 2207/10081* (2013.01); *G06T 2207/10088* (2013.01); *G06T 2207/10132* (2013.01); *G06T 2207/30008* (2013.01); *G06T 2207/30016* (2013.01); *G06T 2207/30204* (2013.01)

(56) References Cited

U.S. PATENT DOCUMENTS

| | | |
|---|---|---|
| 2009/0304252 A1 | 12/2009 | Hyun et al. |
| 2015/0110373 A1 | 4/2015 | Shaham et al. |
| 2017/0103540 A1* | 4/2017 | Brokman ............... A61B 6/032 |

* cited by examiner

METHOD FOR REGISTERING PRE-OPERATIVE IMAGES OF A SUBJECT TO AN ULTRASOUND TREATMENT SPACE

CROSS-REFERENCE TO RELATED APPLICATIONS

This application represents the national stage entry of PCT International Application PCT/IB2016/000627 filed Apr. 25, 2016, which claims the benefit of U.S. Provisional Patent Application 62/152,565, filed on Apr. 24, 2015. The contents of this application are hereby incorporated by reference as if set forth in their entirety herein.

BACKGROUND OF THE INVENTION

The field of the invention is systems and methods for medical imaging and medical image-guided treatment. More particularly, the invention relates to systems and methods for registering pre-operative medical images of a subject to an ultrasound treatment space.

Focused ultrasound ("FUS") is a promising technology that has shown exciting potential for treatment of brain disorders. To date, transcranial FUS has been used for non-invasive surgery for chronic pain, essential tremor, and glioblastoma. These investigations have been based on the thermal ablation of targeted brain tissue using FUS, and have been guided by magnetic resonance imaging ("MRI"), in which MRI thermometry is used to measure temperature elevations during treatment.

There are also non-thermal, cavitation-mediated applications of FUS that are being investigated pre-clinically, such as transient opening of the blood-brain barrier ("BBB") for targeted drug delivery or sonothrombolysis for the treatment of ischemic stroke. For these interventions, MRI is useful for assessing treatment outcome, but is not well suited for real-time monitoring of cavitation processes. Additionally, MRI is not widely accessible and could be prohibitively expensive if frequent treatments are required.

Ultrasound-based monitoring and control of BBB-opening has been demonstrated in preclinical models, and it has been shown that cavitation activity can be mapped in the brain during BBB opening. These studies suggest that low-cost, ultrasound-guided treatment platforms for cavitation-mediated brain therapies may be a viable option for bringing these technologies to routine clinical practice. To practically implement such a system, however, the sound aberrations caused by geometry and heterogeneity of the skull bone must be accounted for and corrected. This is necessary not only for correcting the transmit focus, but also for eliminating image distortion when mapping cavitation activity through the skull.

The gold standard approach to implement these corrections is to use computed tomography ("CT")-derived density and geometry information taken from pre-operative patient CT data to calculate the phase and amplitude corrections necessary to produce a sharp ultrasound focus through the skull.

In current MRI-guided treatments, the pre-operative CT images are registered with the MR-images during the treatment planning stage to bring the CT data into the ultrasound treatment space. A stereotactic frame is used to ensure that the patient's head does not move during the treatment.

Given the limitations of MRI guidance for cavitation monitoring, however, it would be desirable to provide a system and method in which pre-operative CT data can be registered to an ultrasound treatment space without the need for magnetic resonance images.

SUMMARY OF THE INVENTION

The present invention overcomes the aforementioned drawbacks by providing a method for registering a medical image with a treatment space of an ultrasound system. The method includes providing a medical image of a subject that depicts an anatomical feature, such as a skull of the subject. Ultrasound data are acquired from the subject using an array of ultrasound transducer elements that forms a part of an ultrasound system, the coordinate space of which the medical image is to be registered. A time-of-flight measurement is computed for each transducer element from the acquired ultrasound data, and locations defining the surface of the anatomical feature are determined from the provided medical image of the subject. Registration parameters are then optimized from the computed time-of-flight measurements and the described surface of the anatomical feature. The provided medical image is then registered with the coordinate space of the ultrasound system using the determined registration parameters.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 7A shows average displacement (black) and rotation (gray) errors as a function of the skull discretization (surface refinement to 75, 50 and 25% of the initial number of vertices). FIG. 7B shows average displacement (black) and rotation (gray) errors as a function of the weighting factor in the penalty function. FIG. 7C shows average displacement (black) and rotation (gray) errors as a function of the number of elements.

DETAILED DESCRIPTION OF THE INVENTION

Described here are systems and methods for registering pre-operative computed tomography ("CT") data to an ultrasound treatment space for aberration correction and targeting using an array of high-frequency ultrasound elements within the ultrasound therapy array to implement the registration. In combination with cavitation monitoring and control, this ultrasound-based registration of CT data could eliminate the need for MRI during these treatments.

Figure 1:
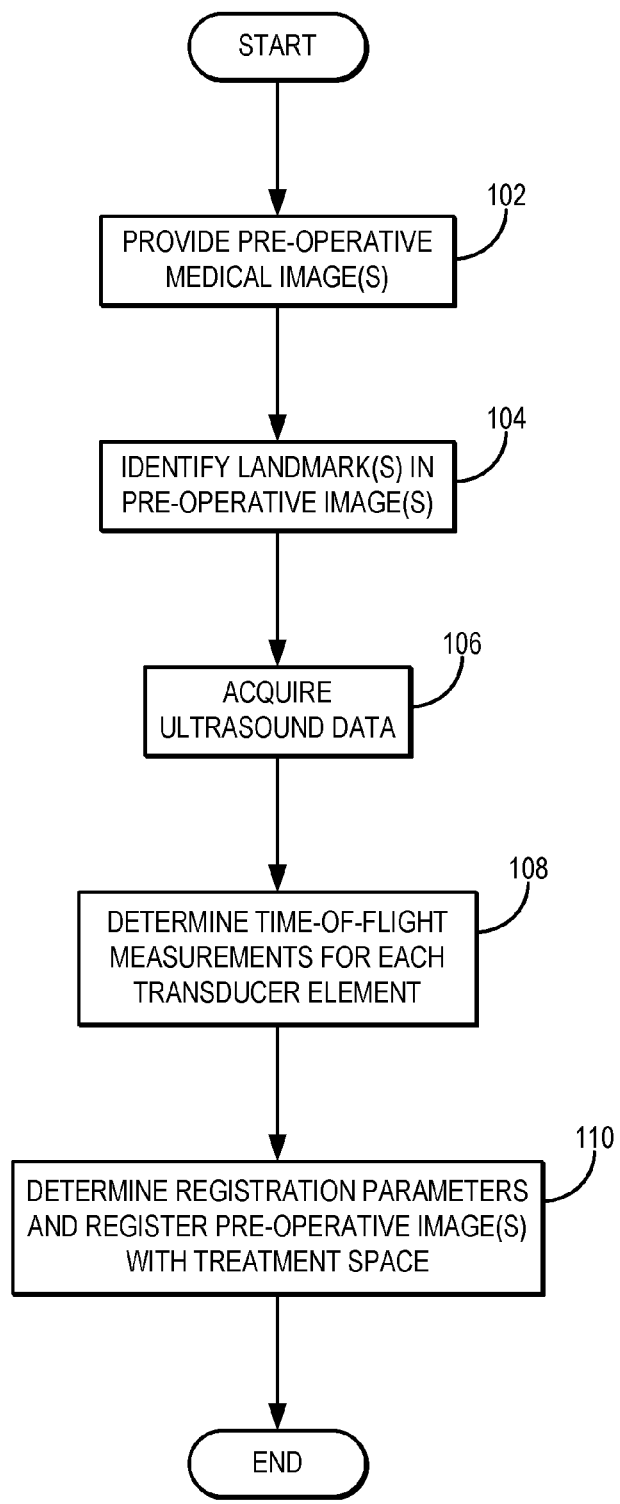
FIG. 1 is a flowchart setting forth the steps of an example method for registering a medical image, such as a computed tomography ("CT") image, with the treatment space of an ultrasound system.

Referring now to FIG. 1, a flowchart is illustrated as setting forth the steps of an example method for registering pre-operative CT data, or other medical image data, to an ultrasound treatment space based on measurement data acquired with an ultrasound transducer array. The method begins by providing pre-operative medical image data of a subject, such as pre-operative CT data, as indicated at step 102. The pre-operative images are then processed to identify landmarks in the images, as indicated at step 104. The landmarks can be anatomical landmarks, including bony surfaces or tissue interfaces, or in some embodiments can include fiducial or other markers that are depicted in the pre-operative images. In one preferred embodiment, the images are CT images that depict the skull of a subject and these CT images are processed to segment the outer surface of the skull. The segmented skull can then be defined in three dimensions by a series of vertices and faces. In some embodiments, these vertices can be downsampled to reduce the computational time.

Next ultrasound data are acquired from the subject, as indicated at step 106. As one, non-limiting example, ultrasound data are acquired using an ultrasound system, such as the example ultrasound system illustrated in FIG. 3, which is described below in more detail. For instance, an electric voltage spike can be transmitted to each ultrasound transducer element in sequence using a pulser/receiver. Once the ultrasound burst hits the skull surface, an echo is generated and received by the transmitting transducer element and captured using an oscilloscope. This process can be repeated for all of the elements in the array.

Then, for each transducer element, i, the time of flight $\Delta t_i$ is determined, as indicated at step 108. As one example, the time of flight can be determined by identifying the rising edge of the echo wavefront. To achieve this, the data can be digitally filtered with a 4th order Butterworth bandpass filter (0.1-20 MHz) and a Hilbert transform taken to extract the signal envelope. The rising edge of the signal envelope can then be located and followed backwards to the closest inflection point. The time of flight, $\Delta t_i$, can be determined as the time associated with the location of this inflection point.

Based on the computed time of flight measurements and on information in the provided pre-operative images, the pre-operative images can be registered to the ultrasound treatment space, as indicated at step 110. As described below, the registration can proceed via one of two methods: a point-based method or a plane-based method. The optimization for either method can be solved using a constrained or unconstrained solver for multiple different starting vectors. The optimization can also be performed without proprietary software by implementing established optimization algorithms (e.g., quasi-newton methods, gradient descent) in C++ or another appropriate programming language.

As one specific and non-limiting example, the optimization problem can be solved in two steps. First, an unconstrained solver can be used to solve for the displacements to center the CT-derived data within the ultrasound space. Then, a constrained solver can be used to solve the full transformation matrix using the solution to the first stage as the initial starting vector, and restricting rotations about and translations along each axis by selected amounts. For example, rotations about each axis can be restricted to ±3 degrees and translations along each axis can be restricted to ±3 mm, respectively.

For both optimization stages, the cost function can be evaluated at each iteration for the transducer elements providing the best fit to the skull surface. This can be done to avoid errors in the calculation of $\Delta t_i$ for some elements biasing the optimization results. For example, for elements near the top of a hemispherical dome array, scattering may result in an artificially shortened $\Delta t_i$.

Figure 2A:
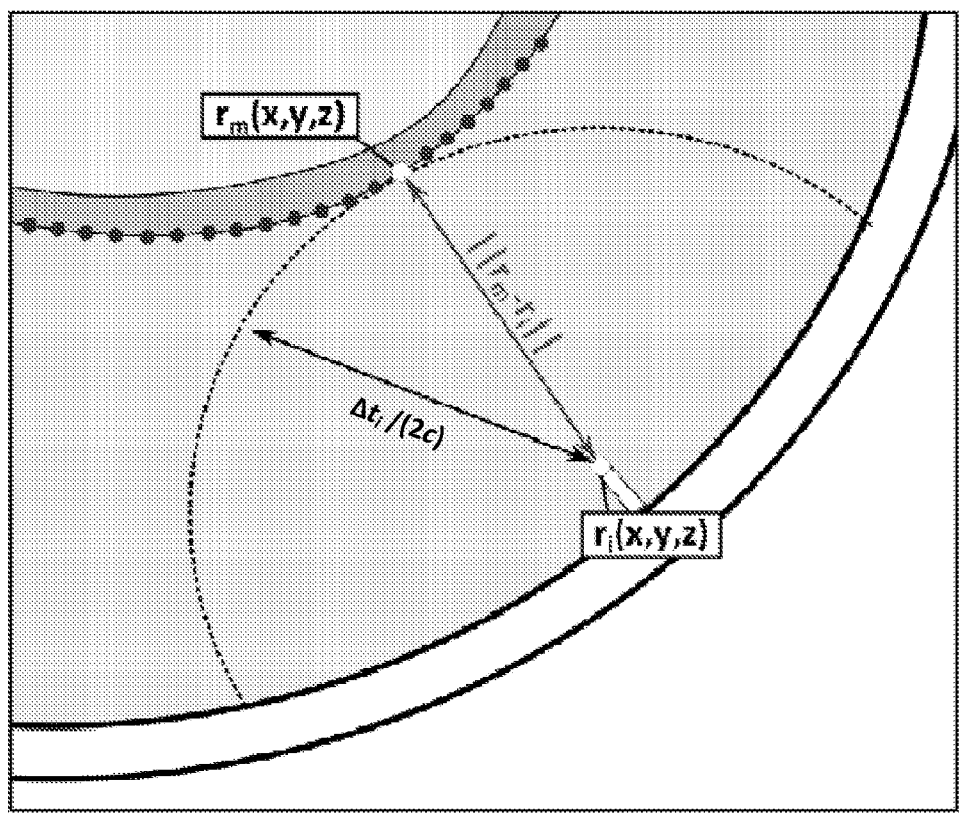
FIG. 2A is an illustration showing a bounding spherical surface centered at transducer element $r_i$ and having radius $\Delta t_i/2c$, and the skull surface positioned so that the distance between the bounding surface and a point, m, on the skull surface is minimized.
Figure 2B:
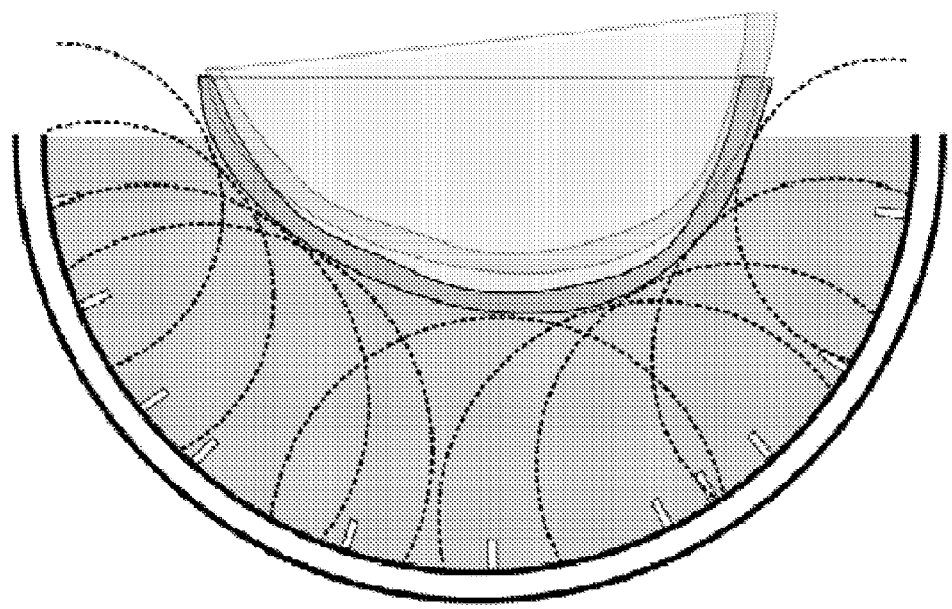
FIG. 2B is an illustration showing an optimal orientation of the skull, where the distance between the bounding surface and a point on the skull surface is minimized for all elements, and where a transparent overlay illustrates a sub-optimal iteration of the point-based optimization technique described here.

In the point-based method, the distance to the point on the skull where the first reflection of the sound occurred is determined from the previously calculated time of flight measurements. As illustrated in FIG. 2A, a point on the skull surface could then be assumed to fall on a spherical surface centered about the i$^{th}$ transducer element and having radius, $\Delta t_i/(2c)$, where c is the speed of sound. For all transducer elements, the skull position within the dome is the position where the skull sits on the multiple spherical bounding surfaces, as shown in FIG. 2B.

Given the CT and ultrasound data, the transformation matrix T(x), where {x} is a vector containing three Euler angles and displacements along the three Cartesian directions, that transforms the CT data into the ultrasound coordinate space can be determined. The solution takes the form of an optimization problem where {x} is the vector of values that minimizes the cost function:

$$x = \mathrm{argmin}\left(\sqrt{\frac{\sum_{i=1}^{N}(R_i(x)+P_i(x))^2}{N}}\right); \quad (1)$$

where $R_i(x)$ is the distance between the spherical control surface for the i$^{th}$ element and the closest point on the skull surface, and $P_i(x)$ is a penalty function. The distance term, $R_i(x)$, can be expressed as:

$$R_i(x) = \min_m \left| \|T(x)r_m - r_i\| - \frac{\Delta t_i}{2c} \right|; \quad (2)$$

where $r_m$ is a vector describing the location of a point {m} on the skull surface, $r_i$ is a vector describing the location of i$^{th}$ transducer element, and $\|\cdot\|$ represents the Euclidean norm. The vector $r_m$ can be defined based on the landmarks identified in the pre-operative images. As described above, these landmarks can be defined by segmenting the skull surface from the images, or based on fiducial or other markers that are positioned on the subject and depicted in the pre-operative images.

The penalty function, $P_i(x)$, is double valued, having a value of zero when the skull sits above the spherical surface, and having the value of the distance the skull has penetrated the surface, times a weighting factor a, if any points on the skull surface lie closer to the $i^{th}$ transducer element than the radius of the bounding surface determined from the ultrasound measurements. Mathematically, this can be expressed as, $$P_i(x) = \begin{cases} |p_i(x)|, & p_i(x) < 0 \\ 0, & p_i(x) \geq 0 \end{cases} ; \quad (3)$$

$$p_i(x) = a \cdot \min_m \left\{ \|T(x)r_m - r_i\| - \frac{\Delta t_i}{2c} \right\}. \quad (4)$$

The second method for determining the registration between the medical image and the ultrasound treatment space is a plane-based method. The cost function in this plane-based method is the same as in the point-based method, but $R_i(x)$ and $p_i(x)$ are modified such that they describe the distance between a face on the skull and the spherical control surface for the $i^{th}$ transducer element. The distance term, $R_i(x)$, can then be expressed as, $$R_i(x) = \left| \frac{n_{mix}r_{ix} + n_{miy}r_{iy} + n_{miz}r_{iz} + d_{mi}}{\|n_{mi}\|} \right| - \frac{\Delta t_i}{2c} ; \quad (5)$$

where the first term in the equation represents the distance between the $i^{th}$ receiver and the face $m_i$; $n_{mi}$ is the normal of face $m_i$; and $d_{mi}$ is a constant in the equation for the plane on which face $m_i$ lies. Face $m_i$ is the face on the skull surface for which the distance between the center of the face and the spherical bounding surface of the $i^{th}$ receiver is minimized; that is, $$m_i = \operatorname{argmin} \left| \|T(x)\langle r \rangle_m - r_i\| - \frac{\Delta t_i}{2c} \right|. \quad (6)$$

In this case, the center of face $m_i$ is described as the average of the vertices of the face, $\langle r \rangle_m$. The function $p_i(x)$ can then be written as, $$p_i(x) = a|R_i(x)| \quad (7).$$

As mentioned above, the optimization for either the point-based or the plane-based method can be solved using a constrained or unconstrained solver for multiple different starting vectors.

Figure 3:
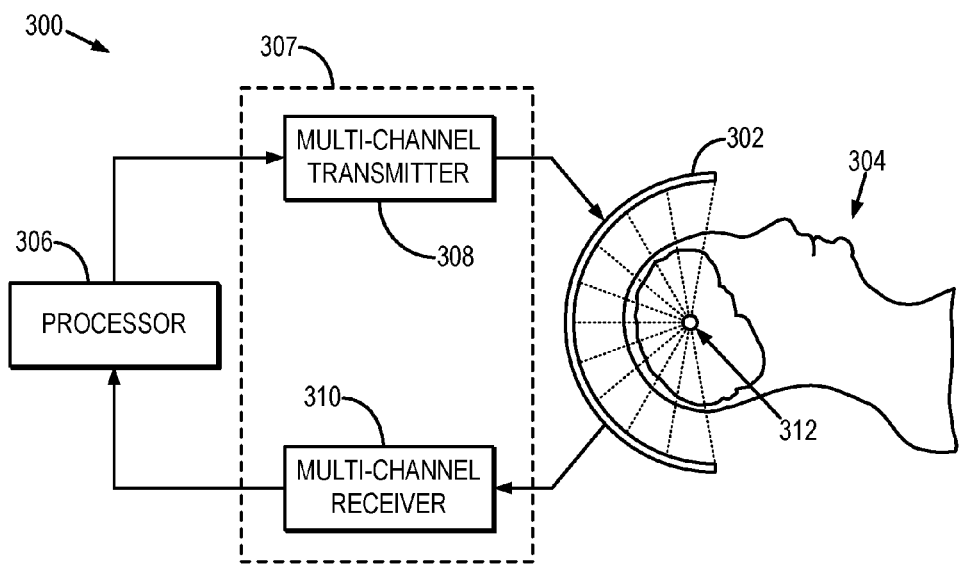
FIG. 3 is a block diagram of an example of an ultrasound system that can implement the methods described here.

By way of example, the method of the present invention can be carried out using an ultrasound system such as the one illustrated in FIG. 3. The ultrasound system 300 generally includes a transducer array 302 that is capable of delivering ultrasound to a subject 304 and receiving responsive signals therefrom. For brain applications, the transducer array 302 is preferably configured to surround an extent of the subject's head. For example, the transducer array 302 may be an approximately hemispherical array of transducer elements.

The ultrasound system 300 also generally includes a processor 306 that is in communication with a pulser/receiver 307, which may include a multi-channel transmitter 308 and a multi-channel receiver 310. The multi-channel transmitter 308 receives driving signals from the processor 306 and, in turn, directs the transducer elements of the transducer array 302 to generate ultrasound energy. The multi-channel receiver 310 receives acoustic signals during and/or after sonications and relays these signals to the processor 306 for processing in accordance with embodiments of the present invention. The processor 306 may also be configured to adjust the driving signals in response to the acoustic signals received by the multi-channel receiver 310. For example, the phase and/or amplitude of the driving signals may be adjusted so that ultrasound energy is more efficiently transmitted through the skull of the subject 304 and into the target volume-of-interest 312. Furthermore, the acoustic signals may also be analyzed to determine whether and how the extent of the focal region should be adjusted.

By way of example, the transducer array 302 may be an approximately hemispherical phased array with multiple transmit-receive ultrasound elements sparsely distributed in such a manner that the variation in the distance between elements is maximized. The diameter of the array 302 may be, for example, 30 centimeters. The array 302 may contain, for example, 128, 256, or more elements that are mounted on a hemispherical surface.

As one non-limiting example, the transducer array 302 can be a sparse hemispherical ultrasound transducer array, such as an array of 128 lead zirconate titanate ("PZT") transducer elements fabricated and installed on the inner surface of a 30 cm diameter hemisphere. The elements in such an array can be constructed as squares with dimensions of 2×2 mm$^2$ and center frequencies of approximately 11 MHz. Electrical connections in the transducer array 302 can be made by soldering to the element electrodes.

The transducer elements in the transducer array 302 can be backed using a 3:1 (by weight) mixture of PZT powder (Del Piezo Specialties, LLC., West Palm Beach, Fla., USA) and epoxy (301 epoxy, Epoxy Technology Inc, Billerica, Mass., USA) in order to improve the transducer bandwidth. In some configurations, this backing layer can be approximately 1 cm thick, with a bottom surface that is angled to prevent reflection of sound back towards the transducer element.

The transducer array 302 can be configured such that the receiver elements are sparsely distributed in a pseudo-random configuration over a whole hemisphere to optimize the imaging resolution; although, it is contemplated that the placement (or the number of elements) may not be critical as long as adequate sampling of the skull surface can be obtained. In an example of such a configuration, the transmit elements can be selected as a subset of all of the elements in the array 302. For instance, the array may contain 1372 transducer elements, of which only 128 are transmit elements. The center frequency of the transmit array can be selected to be sufficiently low so as to undergo minimal distortion and attenuation through the skull bone.

Thus, an ultrasound-based registration method is provided to register medical images, such as CT skull data, to an ultrasound treatment coordinate space. The method provides significant benefits for the development of a low-cost, transcranial ultrasound treatment platform.

Example: Numerical Simulations

A previously developed transcranial ultrasound propagation model based on ray-acoustics was employed to assess the transmit focusing error resulting from imperfections in the US-based registration. The location of the hippocampus within the brain region of five triangulated skull meshes was targeted in silico using a clinical transcranial phased array (ExAblate 4000, InSightec, Haifa, Israel) applicator (1024 elements, 1 cm×1 cm squares, 30 cm diameter array aperture). The phases used to target the hippocampus were determined from the US-registered data, and were applied to landmark-registered (gold-standard) skull configurations to determine the impact of the misalignment on trans-skull focusing. Two factors were expected to contribute to the overall focusing error: the anatomical target being shifted on the planning (US-registered) images relative to its true position, and the cranial bone being shifted in the calculation of the skull-related phase corrections. The simulations were performed at 230 and 650 kHz, and both the peak pressure and positional error were calculated relative to the case where no registration error was present.

Example: Results

Figure 4:
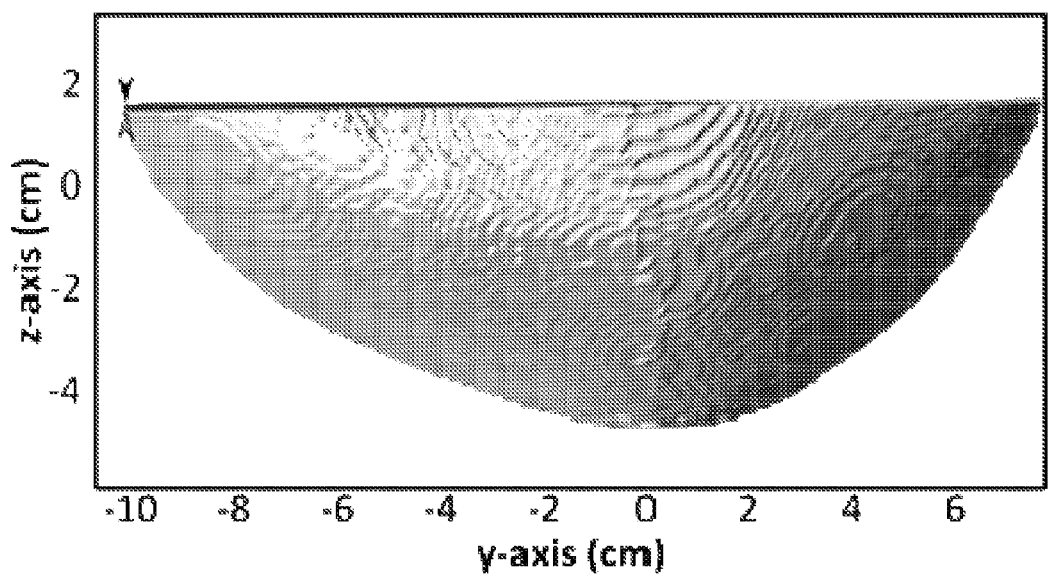
FIG. 4 is an example of landmark-registered (black) and US-registered (gray) data from a skull in an example study (Skull #1) in the reference frame of the US array. The arrowheads highlight a small rotational error.

Of the 128 elements, 96 detected strong echoes from the skull. The remaining 32 elements produced low or no signal. It is contemplated that in some cases this may have been due to non-normal angles of incidence on the skull resulting in the sound being reflected away from the element. The optimization algorithm described above was run using the data from the 96 elements producing strong signals, and at each iteration summing the cost function across the 64 elements yielding the best fit, as described above. An example US-registered skull is shown compared to the landmark-registered data in FIG. 4.

Figure 5:
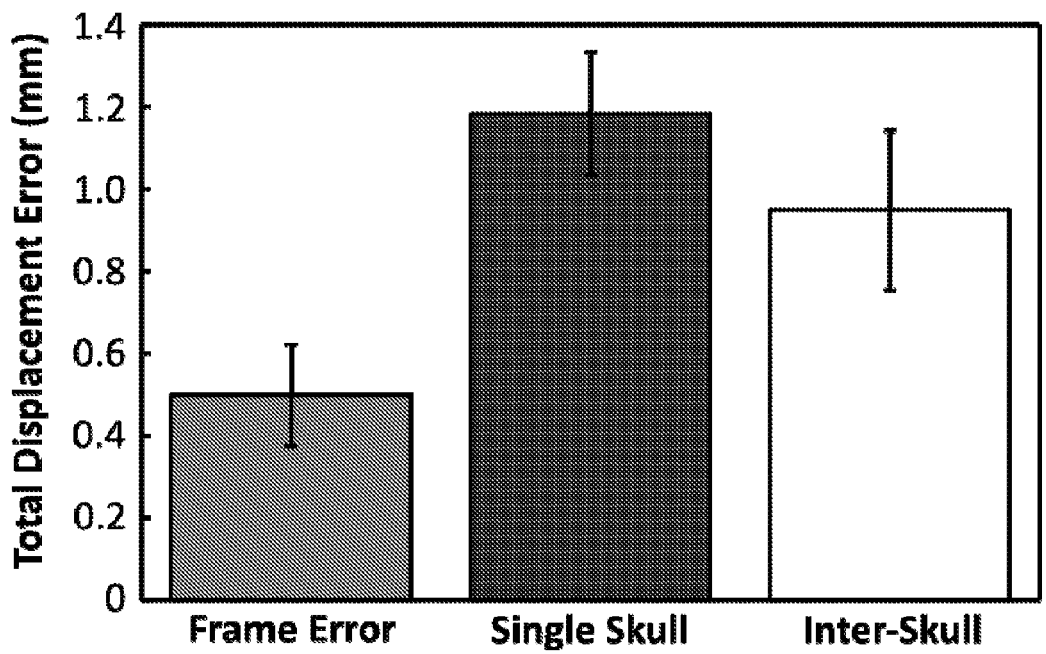
FIG. 5 shows results from an example study and particularly shows average displacement error (mean±s.d.) associated with an experimental fixture (placement reproducibility), multiple measurements of the same skull (skull #5), and measurements across multiple skulls (inter-skull).
Figure 6:
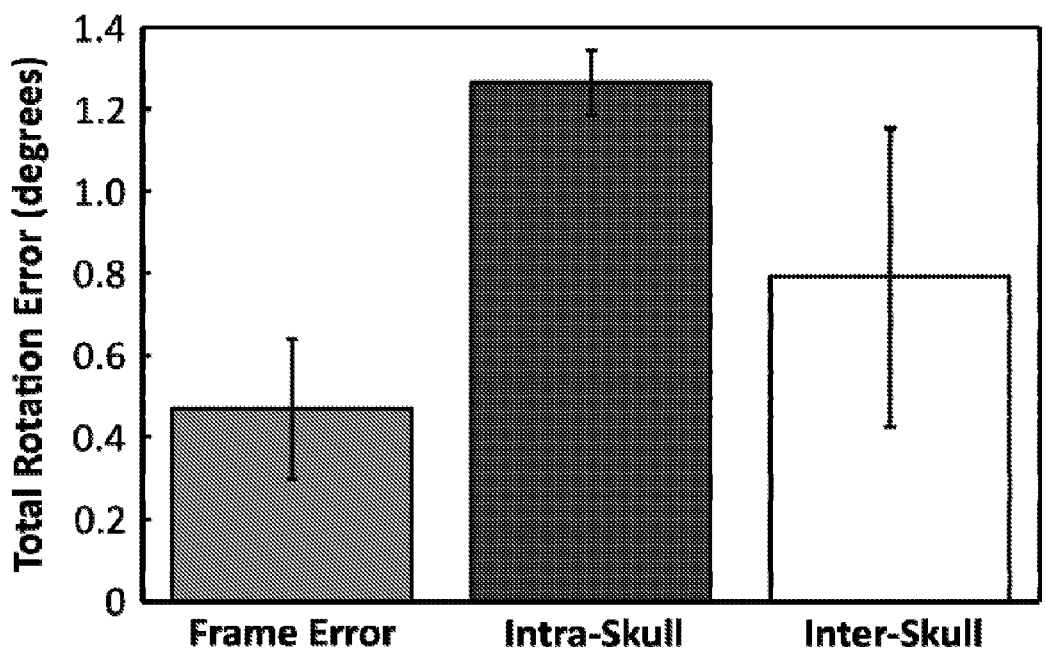
FIG. 6 shows results from an example study and particularly shows average rotation error (mean±s.d.) associated with the experimental fixture (placement reproducibility), multiple measurements of the same skull (skull #5) and measurements across multiple skulls (inter-skull).

FIGS. 5 and 6 show the absolute displacement errors and absolute rotational errors associated with the experimental fixtures (frame error), across multiple CT datasets from the same skull and across multiple different skulls (inter-skull mean). The frame error was calculated using the landmarks on the array frame to register the repeated CT data sets from Skull #5 to the same coordinate space. The skull plate was then registered across the data sets using holes drilled into the plate as references. The frame errors (0.50±0.12 mm; 0.47±0.17 degrees) thus represent the possible differences in the true orientation of the skull between the US and CT measurements.

The displacement and rotation errors associated with repeat measurements of one skull were determined by registering the same US data to the three different CT stacks obtained for Skull #5. With average errors of 1.18±0.15 mm and 1.26±0.08 degrees, Skull #5 had the highest registration error of all the skulls. The low intra-skull standard deviations show that the registration errors did not vary greatly across different CT datasets of the same skull. Across all skulls (using the mean values for Skull #5), on average sub-millimeter (0.95±0.20 mm) and sub-degree errors (0.79±0.36 degrees) were obtained, but larger standard deviations were observed, particularly for the rotational error.

Figures 7A, 7B, 7C:
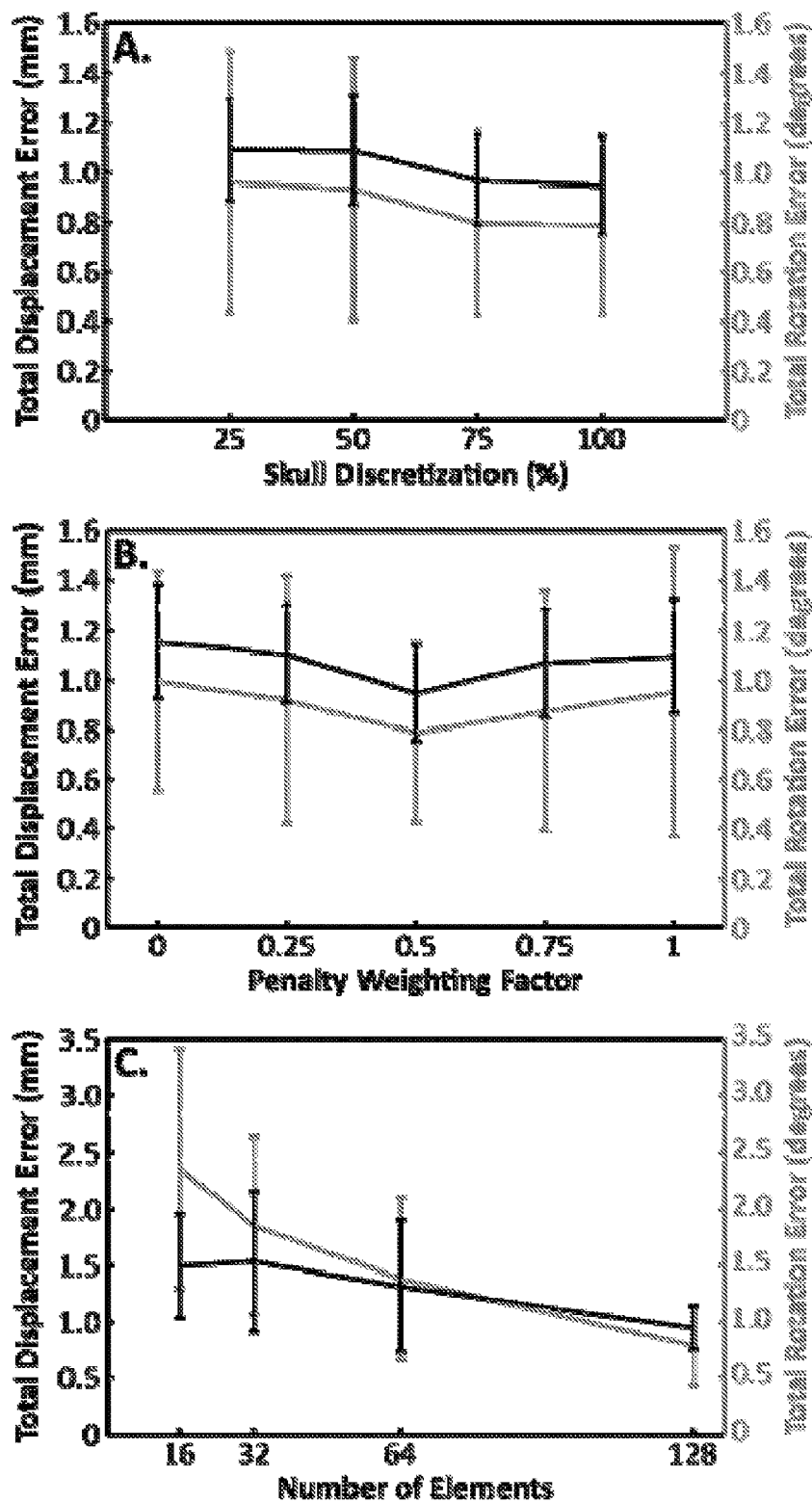
FIGS. 7A-7C show results from an example study and particularly show average (mean±s.d.) displacement (black) and rotation (gray) errors across the five skulls used in the study.

FIGS. 7A-7C show the dependency of this registration scheme on different algorithm parameters averaged across the five skulls. In FIG. 7A, the impact of the skull surface discretization from the CT data is shown. The results are expressed in terms of a percentage of the initial number of vertices, with 100 percent corresponding to no refinement of the surface (10.2±0.6×104 vertices, 0.27±0.06 mm$^2$ face area). The results show a small increase in the mean errors with decreasing discretization. Even when the number of vertices is reduced to 25 percent there was little significant difference in the average errors, (displacement: p=0.35, rotation: p=0.30; two-tailed, paired t-test) although the standard deviation of the displacement errors increases by 46 percent, showing greater variability in the results.

In FIG. 7B, the effect of the penalty weighting factor, a, is shown. Only a modest effect was seen, with a slight, but not significant (displacement: p=0.23, rotation: p=0.31) improvement in the average errors across the skulls at the default value of a=0.5, compared with a=0.

FIG. 7C illustrates the errors as a function of array elements. For the full array (128 elements), only 75 percent (96) of the elements produced usable signals and the optimization cost function was summed across 50 percent (64). To examine the impact of smaller arrays, subarrays were simulated, using 64, 32 or 16 of the elements from the full array, sampled evenly across the array. The same ratios as the full array were maintained. That is, for a nominally 64 element array, 25 percent of the elements were discarded due to poor signal quality (48 elements remaining) and the cost function was summed across 50 percent (32 elements). Reducing the number of elements by half increased the displacement and rotation errors by 39 and 75 percent, respectively, but without statistical significance (displacement: p=0.19, rotation: p=0.14). Although the displacement error did not quite reach a statistically significant difference from the full array (p=0.06 for 16 elements), the rotational error increased significantly when the array was reduced to 32 elements (p=0.01) and was three-fold higher for 16 elements than for the full array.

The results of the numerical simulations are summarized in Table 1, which shows focal pressure and positional shift due to skull-array misregistration relative to the ideal case of perfect registration. Results are shown for 230 and 650 kHz. The targeting error is the shift of the anatomical target due to the registration error.

TABLE 1

Simulation Results

| Skull | Pressure Ratio (%) (230 kHz/650 kHz) | Focal shift (mm) (230 kHz/650 kHz) | Targeting Error (mm) |
|---|---|---|---|
| 1 | 100/99 | 0.6/0.7 | 0.7 |
| 2 | 99/99 | 0.8/0.9 | 0.8 |
| 3 | 99/99 | 0.9/1.0 | 1.0 |
| 4 | 99/99 | 1.2/1.0 | 1.0 |
| 5(1) | 99/99 | 1.0/1.0 | 1.0 |
| 5(2) | 99/99 | 1.1/1.2 | 1.2 |
| 5(3) | 99/98 | 1.2/1.3 | 1.3 |

Using the registration errors obtained for each skull, a mean targeting error of 0.97±0.22 mm at 230 kHz (1.01±0.20 mm at 650 kHz) occurred, while the focal pressure was reduced by 1.0±0.6% at 230 kHz (1.1±0.4% at 650 kHz) on average.

Figure 8:
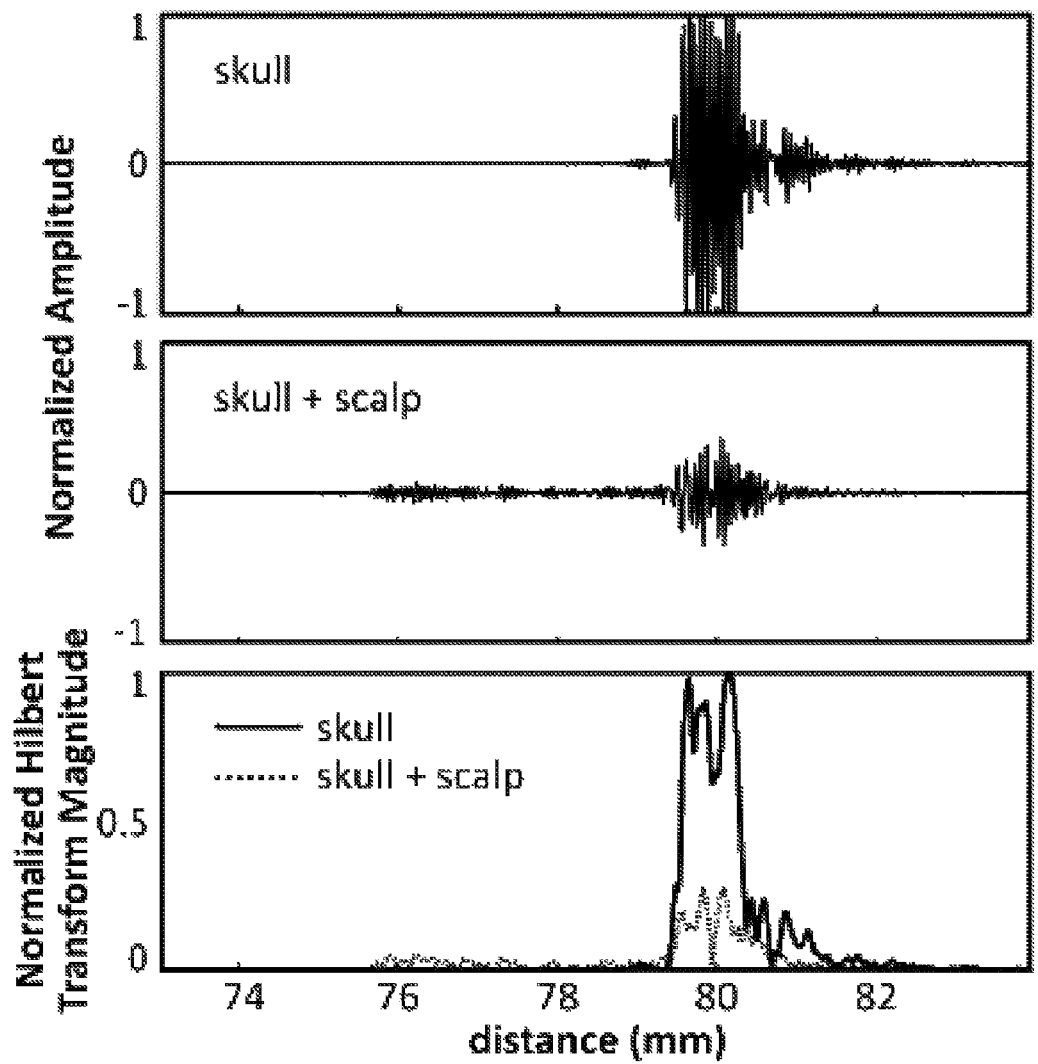
FIG. 8 shows example echoes from a skull with and without the scalp in place (top two panels). The bottom panel of FIG. 8 shows the corresponding Hilbert transform magnitudes for the two cases.

FIG. 8 shows example echoes from a single channel on one skull, with and without the scalp. Although attenuated, the echo from the skull bone can be clearly seen. Also shown are the magnitude of the Hilbert transform for each case, showing a clear rising edge at the tissue-skull interface. From the echo data the scalp thickness at this location was estimated to be about 3.7 mm. This is within the reported range of scalp thickness for adults (3-5 mm). At the cut edge, the scalp used in this study was measured with Vernier calipers to be 7.5 mm thick at its thickest point.

Example: Discussion

The results of this study show that the methods described here can register pre-operative CT-data to the US coordinate space with accuracy on the order of 1 mm/1 degree. For practical implementation, it appears that 128 elements is sufficient, even considering that some elements may not provide useable signals, as was the case in the example study. It is contemplates that more complex algorithms that use triangulation of signals received by surrounding elements may be used to recover information from some of the elements where the transmitted sound is not reflected back to the element, but scattered elsewhere in the dome.

The methods described here are two possible implementations to register CT images of the skull to discrete ultrasound measurements of the skull surface. This method could also be readily adapted to register other 3D data sets of the skull, such as MRI, to ultrasound data. The point-based method described above is computationally faster than the plane-based method, but is more likely to converge to a local minimum rather than a global minimum, particularly if the number of vertices describing the skull surface is downsampled.

Several modifications to the methods described here are possible and will be appreciated by those skilled in the art. For example, the cost function was described in terms of a root-mean-squared value, but could also be expressed in terms of a linear sum or with individual element weightings. Additionally, the distance term, $R_i(x)$, and the face, $m_i$, were expressed in terms of the minimum of an absolute value, or the distance between the skull vertex or face and the closest point. Alternatively, these terms could be expressed as the absolute value of the minimum of the signed distance. This alternative could be used in place of, or in conjunction with, the penalty term to address penetration of the skull surface through the spherical control surfaces. In this example, a relatively simple method was implemented to make the registration more robust by including only the best 50 percent of the elements. More sophisticated methods, such as M-estimators (e.g., the bi-weight, Talwar) could also be used.

For practical implementations, it is contemplated that 128 transducer elements is sufficient for implementing the registration methods described here, even considering that some transducer elements may not provide useable signals. To account for transducer elements that do not provide good signal, algorithms that use triangulation of signals received by other elements may be used to recover information from some of the transducer elements where the transmitted sound is not reflected back to the element, but scattered elsewhere in the dome. These algorithms could potentially improve the accuracy of the measurements.

The registration methods described here can be advantageously used with cavitation-mediated therapies. However, the methods could also have potential application in thermal therapies if ultrasound-based treatment monitoring techniques, such as local harmonic imaging or ultrasound thermometry, can be robustly implemented transcranially. Additionally, because ultrasound imaging is fast and the data from all transducer elements can be acquired on the order of milliseconds, even if the elements are excited one at a time, the methods described here have the potential to track head motion during treatment, thereby removing the need for a stereotactic frame.

Ultrasound data acquisitions can also be accelerated by transmitting from multiple elements at the same time. It may also be possible to use different frequency transmissions from each of the elements to allow more overlapping transmissions. In practice, a temporary frame may be used during the CT imaging and treatment to provide a rough initial alignment of the two data sets prior to optimizing the registration.

The echo signals from the skull are expected to be significantly larger than that from the scalp. Additionally, it is noted that scalp thickness ranges from approximately 3-5 mm in adults, and at 11.25 MHz the ultrasound wavelength in soft tissue is approximately 0.13 mm, suggesting that the water-scalp and scalp-skull interfaces should be resolvable in the pulse-echo data. Naturally, other frequencies that provide the needed precision in the localization can be used.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for registering a medical image with a treatment space of an ultrasound system, the steps of the method comprising:
  (a) providing a medical image of a subject that depicts an anatomical feature;
  (b) acquiring ultrasound data from the subject using an array of ultrasound transducer elements that forms a part of an ultrasound system;
  (c) computing a time-of-flight measurement for each transducer element from the ultrasound data;
  (d) determining locations associated with the anatomical feature from the provided medical image of the subject;
  (e) determining registration parameters from the computed time-of-flight measurements and the locations determined in step (d); and
  (f) registering the provided medical image with a coordinate space of the ultrasound system using the registration parameters determined in step (e).

2. The method as recited in claim 1, wherein step (e) includes minimizing a cost function that is based at least in part on distances between spherical surfaces centered about each transducer element and the determined locations associated with the anatomical feature.

3. The method as recited in claim 2, wherein the spherical surfaces centered about each transducer have a radius defined by the computed time-of-flight measurement for the associated transducer element.

4. The method as recited in claim 3, wherein the radius of the spherical surface is defined as the computed time-of-flight measurement divided by twice a speed of sound.

5. The method as recited in claim 2, wherein the cost function includes a penalty function that is based in part on the distances between the spherical surfaces centered about each transducer element and the determined locations associated with the anatomical feature.

6. The method as recited in claim 5, wherein the penalty function has a zero value for locations when the anatomical feature is located beyond one of the spherical surfaces.

7. The method as recited in claim 1, wherein step (e) includes minimizing a cost function that is based at least in part on distances between spherical surfaces centered about each transducer element and planar surfaces located on the anatomical feature.

8. The method as recited in claim 7, wherein the spherical surfaces centered about each transducer have a radius defined by the computed time-of-flight measurement for the associated transducer element.

9. The method as recited in claim 7, wherein each planar surface located on the anatomical feature is positioned such that at a distance between a center of the planar surface and a spherical surface is minimized.

10. The method as recited in claim 1, wherein step (d) includes segmenting the provided medical image and determining locations associated with the anatomical feature based on the segmented medical image.

11. The method as recited in claim 1, wherein step (d) includes identifying at least one marker in the provided medical image and determining at least one of the locations associated with the anatomical feature as a location of the at least one marker.

12. The method as recited in claim 1, wherein the anatomical feature is a skull of the subject.

13. The method as recited in claim 12, wherein the provided medical image is a computed tomography image.

14. The method as recited in claim 12, wherein the provided medical image is a magnetic resonance image.

* * * * *